United States Patent [19]
Kahn et al.

[11] Patent Number: 5,861,519
[45] Date of Patent: Jan. 19, 1999

[54] PROPYLENE OXIDE PROCESS USING ALKALINE EARTH METAL COMPOUND-SUPPORTED SILVER CATALYSTS CONTAINING TUNGSTEN AND POTASSIUM PROMOTERS

[75] Inventors: Andrew P. Kahn, Eagleville; Anne M. Gaffney, West Chester, both of Pa.

[73] Assignee: Arco Chemical Technology, L.P., Greenville, Del.

[21] Appl. No.: 862,457

[22] Filed: May 23, 1997

[51] Int. Cl.$^6$ .................................................. C07D 301/10
[52] U.S. Cl. .............................................................. 549/536
[58] Field of Search ........................ 549/536; 502/347

[56] References Cited

U.S. PATENT DOCUMENTS

| | | | |
|---|---|---|---|
| 4,007,135 | 2/1977 | Hayden et al. | 252/467 |
| 4,808,738 | 2/1989 | Lauritzen | 549/536 |
| 4,820,675 | 4/1989 | Lauritzen | 502/216 |
| 5,011,807 | 4/1991 | Hayden et al. | 502/218 |
| 5,145,824 | 9/1992 | Buffum et al. | 502/216 |
| 5,364,826 | 11/1994 | Kemp | 502/315 |
| 5,380,885 | 1/1995 | Kemp | 549/536 |
| 5,387,751 | 2/1995 | Hayden et al. | 549/534 |
| 5,407,888 | 4/1995 | Herzog et al. | 502/317 |
| 5,447,897 | 9/1995 | Kemp | 502/303 |
| 5,486,628 | 1/1996 | Kemp | 549/536 |
| 5,502,020 | 3/1996 | Iwakara et al. | 502/317 |
| 5,504,053 | 4/1996 | Chou et al. | 502/348 |
| 5,625,084 | 4/1997 | Pitchai et al. | 549/536 |

FOREIGN PATENT DOCUMENTS

| | | |
|---|---|---|
| 1282772 | 4/1991 | Canada . |
| 1286687 | 7/1991 | Canada . |
| 0480538 | 4/1992 | European Pat. Off. . |
| 0480539 | 4/1992 | European Pat. Off. . |
| 9501837 | 1/1995 | WIPO . |
| 9613493 | 5/1996 | WIPO . |
| 9713579 | 4/1997 | WIPO . |

OTHER PUBLICATIONS

*Ethylene Oxide Production Silver Catalyst*; Nippon Shokubai Kagaku Kogyo Co. Ltd., Jpn Kokai Tokyo Koho, 81, 105, 750, Aug. 22, 1981 7 pp.

*Primary Examiner*—Ba K. Trinh
*Attorney, Agent, or Firm*—Stephen D. Harper

[57] ABSTRACT

Direct oxidation of propylene to propylene oxide is accomplished using alkaline earth metal compound-supported silver catalysts containing tungsten and potassium promoters. In one embodiment of the invention, the tungsten promoter and the potassium promoter are simultaneously introduced through the use of potassium tungstate. Catalysts of this type exhibit unusually high propylene oxide productivity when carbon dioxide is present in the feedstream.

13 Claims, No Drawings

PROPYLENE OXIDE PROCESS USING ALKALINE EARTH METAL COMPOUND-SUPPORTED SILVER CATALYSTS CONTAINING TUNGSTEN AND POTASSIUM PROMOTERS

FIELD OF THE INVENTION

This invention relates to a process for the direct oxidation of propylene to propylene oxide in the vapor phase using molecular oxygen. In particular, the invention pertains to the use of catalysts comprised of silver supported on certain alkaline earth metal-containing compounds. The performance of the catalysts is improved by incorporating a tungsten promoter together with a potassium promoter. The process is desirably operated using carbon dioxide in the feedstream to optimize propylene oxide selectivity.

BACKGROUND OF THE INVENTION

The direct oxidation of ethylene to ethylene oxide by molecular oxygen is well-known and is, in fact, the method used currently for commercial production of ethylene oxide. The typical catalyst for such purpose contains metallic or ionic silver, optionally modified with various promoters and activators. Most such catalysts contain a porous, inert support or carrier such as alpha alumina upon which the silver and promoters are deposited. A review of the direct oxidation of ethylene in the presence of supported silver catalysts is provided by Sachtler et al. in *Catalyst Reviews: Science and Engineering,* 23 (1&2), 127–149 (1981).

It is also well-known, however, that the catalysts and reaction conditions which are best suited for ethylene oxide production do not give comparable results in the direct oxidation of higher olefins such as propylene. The discovery of processes capable of providing propylene oxide by vapor phase direct oxidation in higher yields than are presently attainable thus would be most desirable.

The use of molybdenum-promoted supported silver catalysts as propylene epoxidation catalysts is described in U.S. Pat. No. 5,625,084. While such catalysts are capable of producing propylene oxide at relatively high selectivities when the feedstream contains carbon dioxide, the rate at which propylene oxide is formed (as measured by the concentration of PO in the reactor effluent) unfortunately is quite sensitive to the carbon dioxide concentration. That is, as increasing amounts of $CO_2$ are introduced into the feedstream, the proportion of reacted propylene being converted to propylene oxide becomes greater but the proportion of propylene in the feedstream which is reacted drops significantly, the net result being that the quantity of epoxide produced per unit volume of propylene processed decreases. It would thus be highly desirable to develop direct oxidation catalysts and processing conditions which will permit propylene oxide productivity to be maintained at high levels over a broad range of carbon dioxide concentrations.

According to U.S. Pat. No. 4,007,135, the addition of a number of elements, in particular one of the group consisting of sodium, cesium, rubidium and potassium in combination with at least one member selected from the group consisting of copper, gold, zinc, cadmium, mercury, niobium, tantalum, molybdenum, tungsten, vanadium, chromium, calcium, magnesium, strontium and barium, improves the properties of alpha-alumina-supported silver catalysts used for the preparation of alkylene oxides and having a silver content between 3 and 15 wt. %. This patent teaches that relatively low concentrations of tungsten (from 0.052 to 2570 ppm by weight, based on the final catalyst) are used for said amounts of silver. However, the patent does not teach which tungsten compounds could be used for such purpose, does not specify the nature of tungsten's alleged effect on the properties of the silver catalysts, and does not provide any working examples showing the use of tungsten-containing catalysts.

U.S. Pat. No. 5,407,888 notes that tungsten-doped silver catalysts have not been used in industrial processes for the preparation of ethylene oxide. According to the patent, the reason for this is that doping with tungsten reduces catalyst activity to such an extent that the high temperatures required for long-term usage of these catalysts cannot be attained in the pressure-water-cooled tube bundle reactors normally used for industrial ethylene oxide production. The patent proposes alternative silver catalysts containing one or more alkali metals and also tungsten as promoters on a porous support substantially consisting of low surface area alpha-aluminum oxide and containing tungsten in a concentration not to exceed 990 ppm weight based on the total catalyst.

Additional publications disclosing tungsten-modified supported silver catalysts include U.S. Pat. Nos. 4,808,738, 4,820,675, 5,011,807, 5,145,824, 5,364,826, 5,380,885, 5,447,897, and 5,502,020, Japanese Kokai No. 81-105,650 (Chem. Abstracts 95:2037182), European Pat. Pub. Nos. 480,538 and 480,539, and International Publication Nos. WO95/01837 and WO96/13493.

SUMMARY OF THE INVENTION

A process for propylene epoxidation is provided wherein a feedstream comprising propylene and oxygen is contacted with a particular type of silver catalyst. The catalyst is comprised of (a) a support; (b) a catalytically effective amount of silver; (c) a promoting amount of a tungsten promoter, and (d) a promoting amount of a potassium promoter. The support is comprised of an alkaline earth metal compound selected from the group consisting of alkaline earth metal carbonates (e.g., calcium carbonate), alkaline earth metal titanates, and mixtures thereof. The potassium promoter is desirably derived from a potassium salt which comprises potassium cation and an oxyanion selected from the group consisting of carbon oxyanions, nitrogen oxyanions, tungsten oxyanions and mixtures thereof. In one embodiment, potassium tungstate is utilized to introduce both the tungsten promoter and potassium promoter. The process is desirably operated with a relatively high proportion of carbon dioxide in the feedstream in order to enhance propylene oxide selectivity. The productivity of the catalysts of this invention (as measured by the rate at which PO is produced) does not decrease when the carbon dioxide concentration in the feedstream is increased to the same extent as that of other metal-promoted supported silver catalysts.

In one embodiment of the invention, the feedstream additionally comprises a nitrogen oxide species and/or an organic halide.

DETAILED DESCRIPTION OF THE INVENTION

The present invention is directed to a process for the vapor phase oxidation of propylene to propylene oxide, i.e., an epoxidation process performed in the presence of an oxygen-containing gas and a particular class of supported silver catalysts.

The support material used in the present invention is selected from alkaline earth metal carbonates, alkaline earth metal titanates, and mixtures thereof. Carbonates suitable for use include inorganic carbonates having a cation which is an alkaline earth metal ion, particularly calcium, strontium, magnesium or barium, with calcium carbonate being most preferred. Alkaline earth metal carbonate supports are described, for example, in Canadian Pat. No. 1,282,772. Alkaline earth metal titanates comprise the class of inorganic substances containing an alkaline earth metal such as barium, strontium, calcium, or magnesium and a titanate species. Suitable alkaline earth metal titanates thus may correspond to the empirical formula $MTiO_3$, $M_2TiO_4$, and $MTi_2O_5$ wherein M preferably =Ba, Sr, Ca, or Mg. Any of the conventional methods for preparing such substances may be utilized. Barium titanate, for example, may be prepared by heating a mixture of the correct proportions of barium carbonate and titanium dioxide at 1300° C. until the reaction is complete. Strontium titanate may be obtained in pure form by calcining the double strontium titanium oxalate precipitate from titanium tetrachloride solution. The calcium titanate can correspond to the compound $CaTiO_3$ (CAS 12049-50-2), which occurs naturally as the mineral perovskite, but which can also be synthesized by heating equimolar amounts of the oxide to 1350° C. The term "calcium titanate" as used herein also embraces the substances having the formula $3CaO \cdot 2TiO_2$ (CAS 12013-80-8) and $3CaO.TiO$ (CAS 12013-70-6). Magnesium titanates include the metatitanate $MgTIO_3$, the orthotitanate $Mg_2TiO_4$, and the dititanate $MgTi_2O_5$.

Such support materials are capable of providing exceptionally high propylene oxide selectivities and have been found to be surprisingly superior to other support materials in this respect. The supports of the present invention may exist in various forms. In one embodiment, the support is one in which the alkaline earth metal compound is the predominate (i.e., at least 50% by weight) or, preferably, substantially the exclusive component of the support (i.e., the support consists essentially of one or more alkaline earth metal compounds). In other embodiments of the invention, the inorganic support material is used in conjunction with a solid substrate, i.e., a subsupport or substructure composed of a more conventional support material, such as alumina (preferably, alpha-alumina). However, the alkaline earth metal compound support material will normally comprise at least 25 weight percent (in most embodiments, at least 35 weight percent) of the finished catalyst.

A granular form of the alkaline earth metal compound support material is preferred in the present invention, particularly when used as the exclusive or predominant component of the support. Alkaline earth metal compound materials suitable for use in the present invention may be commercially obtained as powders which can be converted to the preferred granular form by conventional methods. As described in greater detail below, the granular support may then be impregnated, or coated, with a solution containing a silver compound and thereafter reduced to elemental silver.

Alternatively, as described below, the powdered granular support material may be combined with an appropriate silver-containing solution, such as that used conventionally to impregnate solid supports, to form a slurry or paste. This material may then be dried at a moderately elevated temperature (e.g., 75° C. to 150° C.) and calcined at a higher temperature, such as about 500° C. This results in an alkaline earth metal compound support with silver being supported thereon in its elemental state. The catalyst may then be impregnated with solutions of the tungsten and potassium promoters described in more detail hereafter, if so desired, and thereafter dried. As an alternative, the potassium and tungsten promoters may be dissolved in the same silver-containing impregnation solution used to form the coating paste or slurry with the alkaline earth metal compound material. The potassium and tungsten promoters may also be introduced at different steps of the catalyst preparation.

The support material, before or after incorporation of the silver, potassium promoter and tungsten promoter, can be formed into shaped composites suitable for use in propylene oxide manufacture. The composites may be formed by any suitable technique. For instance, it is possible to form the composites by compressing the support materials into a mold having a desired configuration. The size of the particles may be selected to be appropriate for the formation of the composite and are often in the range of about 0.001 to about 5 millimeters in major dimension.

When coated catalysts, i.e., those catalysts in which the alkaline earth metal compound material is coated on a substructure are employed, a slurry of said material, in either powder or granular form, may be mixed with the particles of substructure support material and thereafter dried. As with the predominant or exclusive alkaline earth metal compound support materials described above, the coated catalysts may also be prepared by using a solution of a silver compound and any promoter or separate solutions of silver compound, tungsten promoter and potassium promoter to form the slurry, followed by suitable drying and calcination.

The surface area of the alkaline earth metal compound support material generally is at least 0.6 $m^2/g$, preferably at least 10 $m^2/g$. However, alkaline earth metal compound support materials having relatively high surface areas (e.g., 50 to 100 $m^2/g$) are also effective for the purposes of this invention. The surface area is measured by the conventional B. E. T. method using nitrogen or krypton described by Brunauer, Emmett and Teller in *J. Am. Chem. Soc.* 60,309–16 (1938).

The support materials used in the present invention may generally be described as porous or microporous and typically have water pore volumes of about 0.05 to 0.80 cc/g.

The supported silver catalysts are typically used as individual particles of irregular shape and size. This is true both for the predominate or exclusive alkaline earth metal compound supports as well as the alkaline earth metal compound-coated supports. However, in some instances the supports, particularly the coated supports, may have a particular shape and size and this is especially true of the subsupports used with the alkaline earth metal compound. Typically the subsupports are formed into aggregates or "pills" of a size and configuration to be usable in tubular reactors. These pills may be formed by conventional extrusion and firing techniques. The pills generally range in size from about 2 mm to about 15 mm, preferably about 3 mm to about 12 mm. The size is chosen to be consistent with the type of reactor employed. For example, in fixed bed reactor applications, sizes ranging from about 3 mm to about 10 mm have been found to be most suitable in the tubular reactors commonly utilized. The shapes of the carrier aggregates useful for purposes of the present invention can vary widely and can be any of the forms conventionally used in the heterogeneous catalyst art.

The alkaline earth metal compound- and alkaline earth metal compound-coated supports may be prepared as indicated above or obtained commercially. The supported catalyst of the present invention may be prepared by any known method of introducing silver and/or a promoter in soluble form to a support. A preferred method of introducing silver to the alkaline earth metal compound support is by an impregnation process in which a soluble silver compound (which can be a salt or complex of silver) in an amount sufficient to deposit the desired weight of silver upon the support is dissolved in a suitable solvent or "complexing/solubilizing" agent. The solution may be used to impregnate the support by immersing the support in the silver-containing impregnating solution and forming a pasty mixture or slurry. The slurry is then dried and calcined by placing the mixture in an oven or furnace at about 100° to about 120° C. for 0.5 to 6 hours and then heating the mixture at a temperature of from about 250° to about 600° C. for another 1 to 6 hours. This procedure accomplishes drying of the alkaline earth metal compound/silver mixture, removes volatile components and reduces the silver present to its elemental form.

The potassium promoter and tungsten promoter may be introduced to the catalyst, either simultaneously or separately, as impregnation solutions in a separate impregnation step or steps. Again, this may be done by any known manner of impregnating a porous material. Conveniently, this may be carried out by placing the catalyst material in a container, evacuating the container and thereafter introducing the solution(s). Alternatively, the support may be sprayed or sprinkled with the impregnating solution(s). The excess solution may then be allowed to drain off or the solvent may be removed by evaporation under reduced pressure at a suitable temperature. The catalyst may then be dried at a moderate temperature (e.g., at 120° C.) in a oven for one-half to five hours. Such a procedure is known as a "sequential" or "consecutive" method of preparation. The alkaline earth metal compound-supported catalyst may also be prepared by a "simultaneous" or "coincidental" method of preparation. With this method, the potassium promoter and the tungsten promoter are included in the silver compound-containing solution used to impregnate the support. In another embodiment of the invention, the support is impregnated with a solution or solutions of silver compound and tungsten promoter, dried and calcined, and then impregnated with a solution of potassium promoter and dried.

The particular silver compound used to form the silver-containing impregnating solution in a solvent or a complexing/solubilizing agent is not particularly critical and any silver compound generally known to the art which is both soluble in and does not react with the solvent or complexing/solubilizing agent to form an unwanted product may be employed. Thus, the silver may be introduced to the solvent or complexing/solubilizing agent as an oxide or a salt, such as nitrate, carbonate, or carboxylate, for example, an acetate, propionate, butyrate, oxalate, malonate, malate, maleate, lactate, citrate, phthalate, fatty acid ester, and the like or combinations thereof. In one embodiment, silver (I) oxide is utilized.

A large number of solvents or complexing/solubilizing agents may be suitably used to form the silver-containing impregnating solution. Besides adequately dissolving the silver or converting it to a soluble form, a suitable solvent or complexing/solubilizing agent should be capable of being readily removed in subsequent steps, either by a washing, volatilizing or oxidation procedure, or the like. The complexing/solubilizing agent, preferably, should also permit solution to provide silver in the finished catalyst to the extent of preferably about 10 to about 60 percent silver, based on the total weight of the catalyst. It is also generally preferred that the solvents or complexing/solubilizing agents be readily miscible with water since aqueous solutions may be conveniently employed. Among the materials found suitable as solvents or complexing/solubilizing agents for the preparation of the silver-containing solutions are alcohols, including glycols, such as ethylene glycol, amines (including alkanolamines such as ethanolamine and alkyldiamines such as ethylenediamine) and carboxylic acids, such as lactic acid and oxalic acid, as well as aqueous mixtures of such materials.

Typically, a silver-containing solution is prepared by dissolving a silver compound in a suitable solvent or complexing/solubilizing agent such as, for example, a mixture of water, ethylenediamine, oxalic acid, silver oxide, and monoethanolamine. The solution is then mixed with support particles and drained. Thereafter the particles are suitably dried.

As indicated above, after impregnation, the silver-impregnated support particles are treated to convert the silver compound to silver metal and thereby effect deposition of silver on the surface of the support. As used herein, the term "surface", as applied to the support, includes not only the external surfaces of the support but also the internal surfaces, that is, the surfaces defining the pores or internal portion of the support particles. This may be done by treating the impregnated particles with a reducing agent, such as hydrogen or hydrazine and/or by roasting, at an elevated temperature to decompose the silver compound and reduce the silver to its free metallic state. Certain solubilizing agents such as alkanolamines, alkyldiamines, and the like may also function as reducing agents.

Although at least a catalytically effective amount of silver must be present in the finished catalyst (meaning an amount that provides a-measurable conversion of propylene to propylene oxide), the silver concentration preferably is from about 2 percent to 70 percent, by weight, based on the total weight of the catalyst. More preferably, the silver concentration ranges from about 10 to 60 percent by weight.

It has been discovered that the presence of potassium in the preparation of the supported silver catalyst significantly enhances the efficiency of said catalyst as a propylene epoxidation catalyst. Best results are achieved by introducing the potassium promoter by the use of a potassium salt comprised of potassium cation and an oxyanion selected from the group consisting of carbon oxyanions (e.g., $CO_3^{-2}$, $HCO_3^-$), nitrogen oxyanions (e.g., $NO_3^-$, $NO_2^-$), tungsten oxyanions (e.g., $WO_4^{-2}$, $HW_6O_{21}^{-5}$, $W_6O_{19}^{-2}$, $W_{10}O_{32}^{-4}$, $W_4O_{16}^{-8}$, $H_2W_{12}O_{40}^{-6}$, $W_{12}O_{41}^{-10}$) or mixtures thereof. Illustrative potassium salts suitable for use include, but are not limited to, potassium nitrate, potassium nitrate, potassium carbonate, potassium bicarbonate, potassium tungstate and the like and mixtures thereof.

The efficiency-enhancing potassium salt may be introduced to the catalyst in any known manner. Thus, impregnation and deposition of silver and the potassium salt may be effected coincidentally or sequentially, as described above. The potassium salt may be added to the catalyst after calcination and reduction of the silver compound to metallic form; this is particularly preferred where the potassium salt is potassium nitrate.

In order to perform coincidental impregnation, the potassium salt must be soluble in the same solvent or complexing/solubilizing agent used with the silver impregnating solution. With the preferred sequential procedure in which the silver compound is added first, any solvent capable of dissolving the salt which will neither react with the silver nor leach it from the support is suitable. Aqueous solutions are generally preferred, but organic liquids, such as alcohols, may also be employed. Suitable procedures for effecting introduction of the potassium salt to the solid support are well known in the art.

The potassium salt is used in an amount sufficient to provide a potassium promoter concentration which results in an improvement in one or more of the catalytic properties (e.g., selectivity, activity, conversion, stability, yield) of the supported silver catalyst as compared to a catalyst not containing the potassium promoter. The precise amount will vary depending upon such variables as the composition in the feed stream, the amount of silver contained in the catalyst, the surface area of the support, the process conditions, e.g., space velocity and temperature, and morphology of support. Generally, however, a suitable concentration range of the potassium promoter, calculated as cation, is about 0.15 to about 10 percent, preferably about 0.5 to about 5 percent, by weight, based on the total weight of the catalyst. Most preferably, the potassium promoter level is an amount corresponding to about 1 to about 3 weight percent K.

The other necessary component of the alkaline earth metal compound-supported silver catalysts of this invention is a promoting amount of a tungsten promoter. Other metal promoters such as Mo, Re, Sn and the like may also be present, but the catalyst is capable of operating at relatively high activity and selectivity even when essentially free of metals other than the required silver and tungsten. "Promoting amount" means an amount that works effectively to provide an improvement in one or more catalytic properties of a catalyst as compared to a catalyst not containing the tungsten promoter. The exact form of the tungsten promoter under epoxidation operating conditions is not known. The tungsten promoter, it is believed, is not present on the catalyst in the elemental form since the promoter is applied to the catalyst in the form of a compound such as an ion, salt, or complex and the reducing conditions generally used to reduce the silver to metallic silver are not usually sufficient to reduce the tungsten compound to the elemental form.

It is thought that the tungsten promoter deposited on the support or present on the catalyst is in the compound form, most probably in the form of an oxygen-containing or oxidic compound. In a presently preferred embodiment, the tungsten promoter is introduced to the catalyst in the oxyanionic form, i.e., in the form of an anion, or negative ion which contains oxygen. Examples of oxyanions of tungsten that can be suitably applied include tungstate, ditungstate, paratungstate, other iso- and hetero-polytungstates, phosphotungstate, and the like. The oxyanions can be prepared by the reactive dissolution of various non-anionic tungsten compounds such as the oxides (e.g., $WO_3$) as well as other materials such as acids, carbonates, sulfates, halides, oxyhalides, hydroxyhalides, hydroxides, sulfides, etc., of W. The cation forming the counter ion to the anion in the tungsten compound is suitably ammonium or alkali metal. In one desirable and highly convenient embodiment of the invention, the potassium promoter and the tungsten promoter are simultaneously introduced by means of a potassium salt of tungstate, ditungstate, paratungstate, isotungstate, heteropolytungstate or the like. For example, potassium tungstate ($K_2WO_4$) may be used to impregnate the catalyst. Other potassium salts such as potassium nitrate may advantageously be used in combination with potassium tungstate.

Impregnation of the carrier with the tungsten promoter compound(s) may be done at the same time that the other components of the catalyst are added or before and/or later. In one advantageous and convenient embodiment of the invention, the tungsten promoter compound(s), potassium salt and silver are incorporated into the catalyst simultaneously.

The total amount of tungsten promoter present in or deposited on the support or catalyst is relatively high as compared to previously known supported silver catalysts for ethylene oxide production and ranges from about 0.1 to 10 weight percent W (measured as the element irrespective of the form in which the promoter is present) based on the total weight of the supported silver catalyst. The use of a catalyst containing from 0.5 to 7 wt. % W is particularly advantageous. The degree of benefit obtained within the above-defined limits will vary depending upon particular properties and characteristics, such as, for example, reaction conditions, catalyst preparative techniques, surface area and pore structure and surface chemical properties of the support utilized, silver content of the catalyst, and potassium content of the catalyst.

The tungsten promoter compounds used in the preparation of the instant catalysts are preferably tungsten compounds that can be solubilized in an appropriate solvent. Preferably, the solvent is a water-containing solvent. More preferably the solvent is the same solvent used to deposit the silver and potassium salt.

Propylene and an oxygen-containing gas (i.e., a gas comprising molecular oxygen) are brought together in a reactor in the presence of the previously described catalyst under conditions effective to accomplish at least partial epoxidation of the propylene. Typical epoxidation conditions include temperatures within the reaction zone of the reactor on the order of about 180° to 350° C. (more preferably, 200° to 300° C.) and pressures from about 1 to about 60 atmospheres. To favor high selectivity to epoxide, it is desirable that the feed stream contain carbon dioxide and/or an organic halide (described in more detail hereafter). A gaseous nitrogen oxide species (described in more detail hereafter) is also desirably supplied to the reaction zone within the reactor by introducing said species to the feed-stream containing propylene (fresh and/or recycled) and molecular oxygen.

Examples of nitrogen oxide species suitable for introduction in the feedstream include at least one of NO, $NO_2$, $N_2O_4$, $N_2O_3$ or any gaseous substance capable of forming one of the aforementioned gases, particularly NO and $NO_2$, under epoxidation conditions, and mixtures of one of the foregoing, particularly NO, with one or more of CO, $PH_3$, $SO_3$ and $SO_2$. NO is the most preferred nitrogen oxide species.

The amount of gaseous nitrogen oxide species present is not critical, although it will be highly advantageous to expose the catalyst to the nitrogen oxide species either prior to use (as a preconditioning step) or while being used in the epoxidation process. The optimum amount is determined, in part, by the particular potassium salt and tungsten promoter compound used and the concentrations thereof, and by other factors noted above which influence the optimum amount of potassium and tungsten promoters. Typically, a suitable concentration of the nitrogen oxide species for epoxidation of propylene is about 0.1 to about 2,000 ppm by volume.

The "oxygen" employed in the reaction may be defined as including pure molecular oxygen, atomic oxygen, any transient radical species derived from atomic or molecular oxygen capable of existence under epoxidation conditions, mixtures of another gaseous substance with at least one of the foregoing, and substances capable of forming one of the foregoing under epoxidation conditions. The oxygen is typically introduced to the reactor either as air, commercially pure oxygen or other substance which under epoxidation conditions both exists in a gaseous state and forms molecular oxygen.

The gaseous components which are supplied to the reaction zone, or that region of the reactor where reactants and catalyst are brought together under epoxidation conditions, are generally combined before being introduced to the reactor. If desired, however, such components may alternatively be introduced separately or in various combinations. The feedstream having the particular composition previously described thus may be formed prior to or at the time the individual components thereof enter the reaction zone. The use of the term "feedstream" herein thus is not meant to limit the present process to the embodiment where all of the gaseous components are combined prior to introduction of said components into the reaction zone. The reactors in which the process and catalyst of the present invention are employed may be of any type known to the art. A brief description of several of the reactor parameters which may be used in the present invention is presented below.

In addition to propylene and oxygen, the feedstream also desirably contains a performance-enhancing organic halide such as an alkyl halide. The organic halide is preferably a volatile compound, i.e., a substance which predominantly exists in gaseous form under the temperature and pressure conditions present in the reaction zone. The normal boiling point of the organic halide is most preferably less than about 100° C. at atmospheric pressure. Compounds containing from 1 to 10 carbon atoms are preferred. Most preferably, the alkyl halide is a chloride species. The term alkyl halide includes both saturated and unsaturated halides, such as ethylene dichloride, ethyl chloride, vinyl chloride, methyl chloride and methylene chloride. Preferably, ethyl chloride is employed as the organic halide. Mixtures of different organic halides may be employed. The amount of organic halide employed will vary depending upon a variety of factors, including the concentration of propylene being oxidized, the particular potassium salts and tungsten compounds incorporated into the catalyst, the concentration of nitrogen oxide species as well as other factors noted above as influencing the optimum amount of potassium salt and nitrogen oxide species. However, a suitable range of concentrations for the organic halide in the oxidation of propylene is typically about 0.1 to about 2,000 ppm, more preferably about 20 to 500 ppm by volume, of the feedstream. In addition, a hydrocarbon, particularly a saturated hydrocarbon, such as methane, propane, butane or ethane or mixtures thereof, may be included in the feedstream. The feedstream may also contain a ballast or diluent, such as nitrogen, or other inert gas, particularly when air is used as the source of oxygen. Varying amounts of water vapor may also be present.

Carbon dioxide is also highly desirable to include as a component of the feedstream in the epoxidation process of this invention. The presence of carbon dioxide, within certain limits, has been found to provide surprising improvement in the performance of catalysts within the scope of the invention. In particular, selectivity to propylene oxide generally will increase as the carbon dioxide concentration in the feedstream is increased. As more $CO_2$ is introduced, the rate of PO formation remains relatively constant (especially as compared, for example, to analogous Mo-promoted catalysts)while the rate of $CO_2$ formation (from non-selective over-oxidation of the propylene) decreases. Desirable enhancements are generally observed using 1 to 60 volume % $CO_2$ in the feedstream, with 5 to 50 volume % $CO_2$ being preferred. In one embodiment, carbon dioxide is used as the ballast gas.

In the embodiment of this invention where the feedstream contains only a limited amount of carbon dioxide (e.g., 0 to 10 vol %), an advantage of the process is that less heat needs to be supplied to the reactor to maintain the contents of the reactor at the desired reaction temperature than when the catalyst does not contain a tungsten promoter. In a commercial plant, this will result in a significant decrease in operating utility costs.

The components of the feedstream are most suitably present in the amounts shown in the following table:

| Component | Volume in % (or ppm) for Propylene Oxidation |
|---|---|
| propylene | about 2 to about 50% |
| oxygen | about 2 to about 10% |
| organic halide | 0 to about 2,000 ppm, more preferably, about 20 to 500 ppm |
| nitrogen oxide species | 0 to about 2,000 ppm |
| hydrocarbon other than propylene | 0 to about 80% |
| carbon dioxide | 0 to 60%, more preferably 5 to 50% |
| nitrogen or other ballast gas | remainder. |

Although the present invention can be used with any size and type of vapor phase epoxidation reactor, including both fixed bed and fluidized bed reactors known to the art, it is contemplated that the present invention will find most widespread application in standard fixed bed, multi-tubular reactors such as those now in use as ethylene oxide reactors. These generally include wall-cooled as well as adiabatic or non-wall-cooled reactors. Tube lengths may typically range from about 5 to about 60 feet but will frequently be in the range of from about 15 to about 45 feet. The tubes may have internal diameters from about 0.5 to about 2.5 inches and are expected to be typically from about 0.8 to about 1.5 inches. A plurality of tubes packed with catalyst arranged in parallel within a suitable shell may be employed. GHSV generally ranges from about 500 to about 10,000 $hr^{-1}$. Typically GHSV values range from about 800 to about 3,000 $hour^{-1}$ at pressures from about 1 to about 60 atmospheres, commonly about 1.1 to about 30 atmospheres. Contact times should be sufficient to convert 0.5 to 70%, preferably 5 to 30%, of the propylene.

EXAMPLES

Example 1

This example demonstrates the preparation of a tungsten and potassium promoted silver catalyst supported on calcium carbonate in accordance with the invention.

The following materials were combined in a 16 oz. jar containing 5 ceramic stones: ethylene diamine (20.7 g), distilled water (20.4 g), oxalic acid dihydrate (15.0 g), silver (I) oxide (26.0 g), ethanolamine (7.2 g), a solution of potassium tungstate (5.32 g) in distilled water (5.0 g), and calcium carbonate (34.0 g). The jar was sealed and placed on a ball mill for 4 hours. The mixture was then dried at 110° C. for 1 hour and calcined at 300° C. for 3 hours. Elemental analysis indicated that the supported silver catalyst contained 38 weight % Ag, 2 weight % K and 5 weight % W. The catalyst was pressed and sieved to 14/30 mesh prior to use in epoxidation.

Comparative Example 2

The procedure of Example 1 was repeated, except that 3.2 g of potassium nitrate was substituted for the potassium tungstate. Elemental analysis indicated that the catalyst contained 40 weight % Ag and 2 weight % K.

Example 3

The epoxidation performance of 2 cc of each of the catalysts prepared in Example 1 and Comparative Example 2 was evaluated in a 0.5 inch outside diameter 316 stainless steel tubular reactor at 260° C., 1200 hr$^{-1}$ GHSV and 40 psig. The feedstream contained 10 mol % propylene, 5 mol % oxygen, 200 ppm NO, 50 ppm ethyl chloride and variable amounts of carbon dioxide (the balance being nitrogen). When a W promoter was present in the catalyst (Example 1), the propylene conversion, propylene oxide selectivity and propylene oxide productivity all consistently improved as compared to the catalyst containing no tungsten (Comparative Example 2). This example confirms the beneficial effect of incorporating a W promoter into a silver catalyst prepared using an alkaline earth metal carbonate support. The experimental data are summarized in the following table:

| Catalyst | $CO_2$, mol % | Propylene Conv. % | PO Selectivity, % | PO, ppm | PO Productivity, lb/hr · ft$^3$ |
|---|---|---|---|---|---|
| Example 1 | 0 | 13.3 | 35 | 4800 | 0.86 |
| (5 wt. % W) | 25 | 8.8 | 53 | 4930 | 0.89 |
|  | 50 | 6.8 | 55 | 4090 | 0.73 |
| Example 2 | 0 | 12.6 | 32 | 4210 | 0.76 |
| (0 wt.% W) | 25 | 8.7 | 52 | 4740 | 0.85 |
|  | 50 | 6.3 | 54 | 3750 | 0.67 |

Example 4

This example demonstrates the preparation of a tungsten and potassium promoted silver catalyst supported on calcium carbonate where ammonium paratungstate is used as the source of W and potassium nitrate is used as a source of the potassium promoter. The following materials were combined in a 16 oz. jar containing 5 ceramic stones: ethylene diamine (20.7 g), distilled water (20.4 g), oxalic acid dihydrate (15.0 g), silver (I) oxide (26.0 g), ethanolamine (7.2 g), a solution of ammonium paratungstate (0.5 g) in distilled water (5.0 g), and calcium carbonate (34.0 g). The jar was sealed and placed on a ball mill for 4 hours. The resulting mixture was dried at 110° C. for 1 hour and then calcined at 300° C. for 2 hours. Potassium nitrate (3.2 g) was dissolved in distilled water (50 g) and added to the calcined catalyst to form a slurry. The water was removed using a rotary evaporator and the catalyst dried at 110° C. for 2 hours. Elemental analysis indicated the catalyst contained 39 weight % Ag, 2 weight % K and 0.6 weight % W. The catalyst was pressed and sieved to 14/30 mesh prior to use.

We claim:

1. A process for propylene epoxidation comprising contacting a feedstream comprising propylene, oxygen, carbon dioxide, a nitrogen oxide species and an organic halide at a temperature of from 200° C. to 300° C. with a supported silver catalyst comprised of:
   (a) a support comprised of calcium carbonate wherein calcium carbonate constitutes at least 25 percent by weight of the supported silver catalyst;
   (b) from 10 to 60 weight percent Ag;
   (c) from 0.5 to 7 weight percent W derived from a tungsten compound comprised of a tungsten oxyanion; and
   (d) from 0.5 to 5 weight percent K derived from a potassium salt selected from the group consisting of potassium carbonate, potassium bicarbonate, potassium nitrate, potassium nitrite, potassium tungstate, and mixtures thereof.

2. The process of claim 1 wherein the supported silver catalyst is essentially free of rhenium.

3. The process of claim 1 wherein the tungsten compound and the potassium salt are potassium tungstate.

4. The process of claim 1 wherein the supported silver catalyst is obtained by a method comprising impregnating the support with one or more solutions comprising (a) a silver compound, (b) the potassium salt and, where the potassium salt is other than potassium tungstate, the tungsten compound to form an impregnated support and thereafter reducing the silver compound in the impregnated support to metallic silver.

5. The process of claim 1 wherein the tungsten compound is ammonium paratungstate.

6. The process of claim 1 wherein the potassium salt is potassium nitrate.

7. The process of claim 1 wherein the supported silver catalyst is obtained by a method comprising impregnating the support with one or more solutions comprising (a) a silver compound and (b) the tungstate compound to form an impregnated support, reducing the silver compound in the impregnated support to metallic silver, and impregnating the reduced impregnated support with the potassium salt.

8. The process of claim 1 wherein the support consists essentially of calcium carbonate.

9. The process of claim 1 wherein the supported silver catalyst is comprised of 1 to 3 weight percent K.

10. The process of claim 1 wherein the nitrogen oxide species is NO.

11. The process of claim 1 wherein the organic halide is an alkyl chloride.

12. The process of claim 1 wherein the tungsten compound is selected from the group consisting of ammonium paratungstate, sodium tungstate, potassium tungstate and mixtures thereof.

13. A process for propylene epoxidation comprising contacting a feedstream comprised of propylene, oxygen, carbon dioxide, NO and an alkyl chloride at a temperature of from 200 to 300° C. with a supported silver catalyst comprised of
   (a) a support consisting essentially of calcium carbonate;
   (b) from 10 to 60 weight percent Ag;
   (c) from 0.5 to 7 weight percent W derived from a tungsten compound selected from the group consisting of ammonium paratungstate, sodium tungstate, potassium tungstate and mixtures thereof; and
   (d) from 1 to 3 weight percent K derived from a potassium salt selected from the group consisting of potassium carbonate, potassium bicarbonate, potassium nitrate, potassium nitrite, potassium tungstate and mixtures thereof, wherein said supported silver catalyst is essentially free of rhenium.

* * * * *